US012064383B2

United States Patent
Kokko et al.

(10) Patent No.: US 12,064,383 B2
(45) Date of Patent: Aug. 20, 2024

(54) METHOD FOR REDUCING TISSUE INTERFACE PRESSURE

(71) Applicant: Sizewise Rentals, L.L.C., Eden Prairie, MN (US)

(72) Inventors: Michael A. Kokko, Lyme, NH (US); Spencer C. Brugger, Orford, NH (US); Eric L. Yuan, Lebanon, NH (US); Amaris G. Ajamil, White River Junction, VT (US); Jeffrey J. Chu, Norwich, VT (US); Richard M. Greenwald, Lebanon, NH (US)

(73) Assignee: Sizewise Rentals, L.L.C., Eden Prairie, MN (US)

( * ) Notice: Subject to any disclaimer, the term of this patent is extended or adjusted under 35 U.S.C. 154(b) by 959 days.

(21) Appl. No.: 16/987,757

(22) Filed: Aug. 7, 2020

(65) Prior Publication Data
US 2021/0038455 A1    Feb. 11, 2021

Related U.S. Application Data

(60) Provisional application No. 62/884,448, filed on Aug. 8, 2019.

(51) Int. Cl.
*A61G 7/057* (2006.01)
*A61B 5/00* (2006.01)
*A61G 7/018* (2006.01)

(52) U.S. Cl.
CPC ......... *A61G 7/05769* (2013.01); *A61G 7/018* (2013.01); *A61G 7/05776* (2013.01);
(Continued)

(58) Field of Classification Search
CPC ............... A61G 7/018; A61G 7/05769; A61G 7/05753; A61G 7/05776; A61G 2203/34;
(Continued)

(56) References Cited

U.S. PATENT DOCUMENTS 4,833,614 A    5/1989    Saitoh et al.
5,020,176 A    6/1991    Dotson
(Continued)

FOREIGN PATENT DOCUMENTS

CN    102421403 B  *  5/2013    ............. A61B 5/447
EP    3231407 A1    10/2017
(Continued)

OTHER PUBLICATIONS

Mimura, M. et al., "Mechanism leading to the development of pressure ulcers based on shear force and pressure during bed operations :Influence of body types, body position, and knee position", Wound Repair and Regeneration, 2009, 17, 789-796.
(Continued)

*Primary Examiner* — David R Hare
(74) *Attorney, Agent, or Firm* — Spencer Fane, LLP

(57) ABSTRACT

The present invention relates to the reduction of tissue interface pressure. The present invention provides a method to immerse an individual to a desired depth into a support surface. The method of the present invention maintains a desired level of immersion over time independent of the motion of the individual or changes in the position of the support surface or externally applied loads to the support surface, alone or in combination. The method of the present invention is an improvement to using an individual's weight or height or other sensor to determine inputs to an algorithm for immersing the individual to a certain depth into the surface. No pressure measurements or displacement measurements are required in accordance with the present invention, and the height and weight of the individual is not required.

12 Claims, 8 Drawing Sheets

(52) U.S. Cl.
CPC .............. *A61B 5/442* (2013.01); *A61B 5/447* (2013.01); *A61B 2562/029* (2013.01); *A61G 2203/34* (2013.01); *A61G 2203/46* (2013.01)

(58) Field of Classification Search
CPC .......... A61G 2203/46; A61B 2562/029; A61B 5/442; A61B 5/447; A61B 5/6843; A61H 9/0071; A61H 9/0078; A61H 9/0085; A61H 2201/1645
USPC .......................................................... 5/710
See application file for complete search history.

(56) References Cited

U.S. PATENT DOCUMENTS

| | | | |
|---|---|---|---|
| 5,848,450 A | 12/1998 | Oexman et al. | |
| 7,414,536 B2 | 8/2008 | Call et al. | |
| 7,515,059 B2 | 4/2009 | Price et al. | |
| 7,656,299 B2 | 2/2010 | Gentry et al. | |
| 7,669,263 B2 | 3/2010 | Menkedick et al. | |
| 7,883,478 B2 | 2/2011 | Skinner et al. | |
| 8,031,080 B2 | 10/2011 | Price et al. | |
| 8,102,270 B2 | 1/2012 | Gowda et al. | |
| 8,531,307 B2 * | 9/2013 | Lachenbruch | A61B 5/6892 340/665 |
| 8,539,627 B2 | 9/2013 | Terawaki et al. | |
| 8,698,509 B2 | 4/2014 | Call et al. | |
| 8,745,788 B2 | 6/2014 | Bhai | |
| 8,769,747 B2 | 7/2014 | Mahoney et al. | |
| 8,950,768 B2 | 2/2015 | Nihei | |
| 9,107,511 B2 | 8/2015 | Skinner et al. | |
| 9,320,665 B2 * | 4/2016 | Main | A61G 7/057 |
| 9,348,341 B2 | 5/2016 | Heger et al. | |
| 9,445,751 B2 | 9/2016 | Young et al. | |
| 9,468,307 B2 | 10/2016 | Lafleche et al. | |
| 9,504,620 B2 | 11/2016 | Soltani et al. | |
| 9,737,154 B2 | 8/2017 | Mahoney et al. | |
| 9,848,712 B2 | 12/2017 | Main et al. | |
| 9,901,499 B2 | 2/2018 | Darnold et al. | |
| 10,251,593 B2 * | 4/2019 | Sugla | G16H 40/67 |
| 10,413,464 B2 | 9/2019 | Lachenbruch et al. | |
| 10,729,357 B2 | 8/2020 | Larson et al. | |
| 2001/0029628 A1 | 10/2001 | Ferrand et al. | |
| 2007/0285269 A1 | 12/2007 | Geay | |
| 2008/0005843 A1 * | 1/2008 | Lokhorst | A61G 7/001 297/452.41 |
| 2009/0106905 A1 | 4/2009 | Ochi et al. | |
| 2011/0068939 A1 * | 3/2011 | Lachenbruch | A61G 7/0525 340/626 |
| 2011/0185509 A1 | 8/2011 | Genaro | |
| 2012/0277637 A1 | 11/2012 | Vahdatpour et al. | |
| 2013/0006151 A1 * | 1/2013 | Main | A61G 7/057 600/587 |
| 2013/0340176 A1 | 12/2013 | Stevens et al. | |
| 2014/0101862 A1 | 4/2014 | Misaki | |
| 2014/0223665 A1 * | 8/2014 | Chapin | A47C 27/10 5/710 |
| 2015/0128354 A1 | 5/2015 | Greenstein et al. | |
| 2015/0136146 A1 | 5/2015 | Hood et al. | |
| 2017/0086598 A1 | 3/2017 | Ohno | |
| 2017/0325683 A1 | 11/2017 | Larson et al. | |
| 2018/0014774 A1 * | 1/2018 | Hollopeter | A61B 5/1116 |
| 2018/0027988 A1 | 2/2018 | Poodeh et al. | |

FOREIGN PATENT DOCUMENTS

| | | | |
|---|---|---|---|
| GB | 2568875 A | 6/2019 | |
| WO | WO-9939613 A1 * | 8/1999 | ......... A61G 7/05769 |
| WO | 2009132107 A2 | 10/2009 | |
| WO | WO-2009132107 A2 * | 10/2009 | ....... A61F 13/00051 |
| WO | 2013170335 A1 | 11/2013 | |
| WO | 2015116304 A1 | 8/2015 | |

OTHER PUBLICATIONS

Ceelen, K.K. et al., "Micro-structural analysis of deformation-induced hypoxic damage in skeletal muscle" Biomechanics and Modeling in Mechanobiology. 2008. 7, 277-284.

Loerakker, S., "Aetiology of pressure ulcers", Oct. 2007. (BMTE No. 07.39). Eindhoven University of Technology, Netherlands.

Lowthian, P.T., "Trauma and thrombosis in the pathogenesis of pressure ulcers," Clinics in Dermatology 2005, 23, 116-123.

Mao, C.L. et al., "Update of pressure ulcer management and deep tissue injury", Geriatrics—The Annals of Pharmacotherapy. Feb. 2010, vol. 44, 325-332.

Thomas, D.R., "Prevention and treatment of pressure ulcers: What works? What doesn't?", Cleveland Clinic Journal of Medicine, Aug. 2001, vol. 68(8), 704-722.

Petzold, J., European Search Report for Patent Application No. 20849236.3, dated Jul. 11, 2023, European Patent Office.

\* cited by examiner

METHOD FOR REDUCING TISSUE INTERFACE PRESSURE

CROSS-REFERENCE TO RELATED APPLICATION

This application claims priority to earlier flied U.S. Provisional Patent Application No. 62/884,448, filed on Aug. 8, 2019, the entire contents of which are incorporated herein by reference.

GOVERNMENT LICENSE RIGHTS

This invention was made with government support under award R44NR014388 awarded by the National Institutes of Health. The government has certain rights in the invention.

BACKGROUND OF THE INVENTION

The invention relates to the control of support surfaces to minimize tissue interface pressure. The present invention relates to the field of medical equipment, particularly to support surfaces for prevention and treatment of pressure ulcers. More specifically, the present invention relates to a method of reducing tissue interface pressure (TIP) specifically in areas of the body where pressure ulcers are most likely occur and based on the individual's anatomy. Additionally, the present invention relates to a method of reducing TIP based on other variables such as immersing an individual into a support surfaced, the position of the individual on the support surface, the orientation of the support surface, and other external loads applied to the support surface. Additionally, the present invention relates to a method of further reducing TIP using targeted offloading of pressure in response to a physiological parameter or multiple parameters.

It is well known in the medical field that pressure ulcers are a major problem in hospital and nursing care. In the US alone, pressure ulcers afflict approximately 2.5 million people annually and cause 60,000 deaths. In bedridden or wheelchair confined patients, pressure ulcers are caused by the force of the bed surface or wheelchair pad on the patient. Nurses will utilize a turning scheduled to help alleviate the pressure on specific areas of the body. The fundamental cause of pressure ulcers has been the subject of research studies for decades. It is generally accepted that external mechanical loading is the primary cause, but the actual mechanisms leading to pressure ulcer formation are still unclear. A widely held hypothesis is that tissue compression prevents the blood stream from supplying nutrients and oxygen to a localized area (capillary perfusion) eventually blocking the flow entirely (ischemia). After the load is removed and blood flow returns inflammation and cell damage may become evident as the tissue can no longer function normally (reperfusion injury). The tissue closest to the bone is most susceptible to necrosis, the death of living cells or tissue caused by conditions such as ischemia. Pressure ulcers tend to form at these sites. Thus, pressure relief is the cornerstone of pressure ulcer prevention. In addition to direct pressure or tissue interface pressure (TIP), other ulceration mechanisms are thought to include shear and friction loading. Since both of these variables depend on interface pressure, reducing interface pressure will reduce both shear and friction.

Support surfaces can be characterized as reactive or active. Reactive systems, which change load distribution only with a change in applied load, are typically based upon immersion and envelopment of the individual with respect to the surface. Immersion into the surface and envelopment of the surface material around the body increases the contact area of the body with the surface, which reduces contact pressure. Once immersed and enveloped, however, the pressure applied to the skin and underlying tissues remains constant until the patient moves, the surface is moved, such as might occur if the bed is articulated, or an external load is applied to the surface, such as might occur if an object is placed on the surface or a person sits on the surface. The pressure applied to the skin and underlying tissues may exceed the level at which pressure ulcer formation will occur. Active systems, which can change load distribution independent of applied load, involve periodic redistribution of pressure to the skin and underlying tissues, often via the inflation or deflation of fluid-filled cells or chambers, often air filled, or other relevant technology.

Current reactive and active support surfaces do not necessarily solve the problem that the patient can encounter transient pressure gradients and points of elevated pressure that can contribute to pressure ulcer formation. This may be a result of the load-bearing medium of the mattress not reacting in a linear manner to patient weight, or to the patient moving while on the support surface. The reactive forces generated are not independent of the amount and location of loads across the mattress surface, causing variation in the support and envelopment characteristics of the medium. With passive reactive systems, an incident load can partially collapse the support material in the area surrounding a contact point, degrading load-bearing properties. Typical air mattresses use tubular chambers running across the width of the bed to decouple loadbearing partitions, but distortion can still take place along the tube cross section and length.

Pressure redistribution is one of several factors known to prevent pressure ulcers and aid in treatment. Pressure redistribution support surfaces include foam, air inflatable, alternating pressure, low air loss, and air fluidized (AFT of "sand bed") therapies.

Clinicians report dissatisfaction with the cost, usability, and patient experience of existing support surface products for treatment of decubitus ulcers and providing post-flap/graft surgery care. There is a need for a support surface designed to intelligently and selectively offload high-risk tissue. Such a system can improve patient care and reduce caregiver workload and fatigue. The key property of a therapeutic support surface for treatment of pressure ulcers is its ability to maximize and preserve contact with the body to distribute the patient's weight evenly over a broad surface and to eliminate excessive tissue interface pressure on bony protuberances where ulcers generally occur. In addition, effective management of the temperature and moisture of the tissue-surface environment is considered essential for preventing or healing pressure ulcers, and improving patient comfort.

Most prior art methods for immersion of the body or body part of a patient require or incorporate sensors, measurements, or external inputs as part of the immersion schema. For example, the individuals' weight and or height may be required to be entered or measured. An alternative approach is to sense pressure and pressure changes in a fluid-filled chamber on which an individual is sitting or lying, and to immerse the patient to a set pressure. Another alternative approach is to use displacement monitoring means to quantify a distance between the patient and the bottom of the support surface. In some cases, a pressure mat is utilized to drive the immersion process. These pressure mats may actually change the characteristics of the support surface itself compared to when a pressure mat is not present.

Therefore, there is a need for a method to immerse an individual into a support surface without the need for sensors, the individual's weight or height or pressure or displacement measurements.

SUMMARY OF THE INVENTION

The present invention relates to the reduction of TIP. The present invention involves a method to immerse an individual to a desired depth into a support surface. The present invention involves maintaining a desired level of immersion over time independent of the motion of the individual or changes in the position of the support surface or externally applied loads to the support surface, alone or in combination. The present invention is a novel alternative to using an individual's weight or height or other sensor means to determine inputs to an algorithm for immersing the individual to a certain depth into the surface.

Therefore, an object of the method of the present invention is to immerse an individual to a desired depth into a support surface without requiring pressure measurements or displacement measurements.

A further object of the present invention is to immerse an individual to a desired depth into a support surface without requiring the height and weight of the individual.

BRIEF DESCRIPTION OF THE DRAWINGS FIGURES

FIG. 1 is graph showing percent immersion over time for a number of different weight ranges;

FIG. 2 is a graph showing percent immersion over time showing that after quickly exhausting for 45 seconds, all subjects again fall between 40 and 50% immersion;

DESCRIPTION OF THE INVENTION

The novel method of the present invention is directed to exhausting fluid (e.g., air) from the fluid chambers of a support surface from a known starting pressure in each chamber for a fixed time to achieve a desired level of immersion into the surface. Chambers in contact with the body that have higher tissue interface pressure will move fluid volume due to the increased external pressure created by the body at a higher rate than bladders that have lower tissue interface pressures as dictated by Bernoulli's principle. This approach is intended to reduce the complexity of other approaches to immersion that rely on external inputs or sensors that are monitoring pressure or other measures used to define a desired immersion level. In order to define the fixed time to exhaust the fluid in the cells of the support surface, characterization of various elements of the support system, including but not limited to, internal flow rates, support surface materials, pressure changes during immersion, weight, position on the surface, and other variables via empirical testing using human subjects and test dummies that encompass the various patient characteristics specified for the particular support surface application. This includes the weight range of individuals over which the support surface is intended for use. Multivariate regression, curve fitting, and other analytic techniques are employed to model the various parameters to quantify an exhaust time for the system to achieve a desired immersion depth. In this way, while sensors and individual weight are parameters used to characterize the system, these variables are not required to be input or measured individually during the immersion process, which for this application is called Timed Exhaust.

Experimental data demonstrated that the level of immersion for a Timed Exhaust is independent of the height or weight of the individual for the specific surface utilized and the modeling performed on that support surface. Using Timed Exhaust, individuals were immersed to a desired immersion depth within a depth range, such as ±12.7 mm. The desired immersion depth can be selected. For example, the immersion depth can be 25.4 mm off of the top of the deck of the bed frame below the support surface, for any chamber fluid volume.

The Timed Exhaust method can use different fluid exhaust times for different chambers within the support surface. For example, in a support surface where there are multiple fluid chambers, and those multiple fluid chambers are assigned to zones of the support surface (e.g., top, middle, other), the Timed Exhaust for the top zone could be for 35 seconds, the middle zone for 25 seconds, and the other zone for 45 seconds resulted in the desired immersion.

Figure 1:
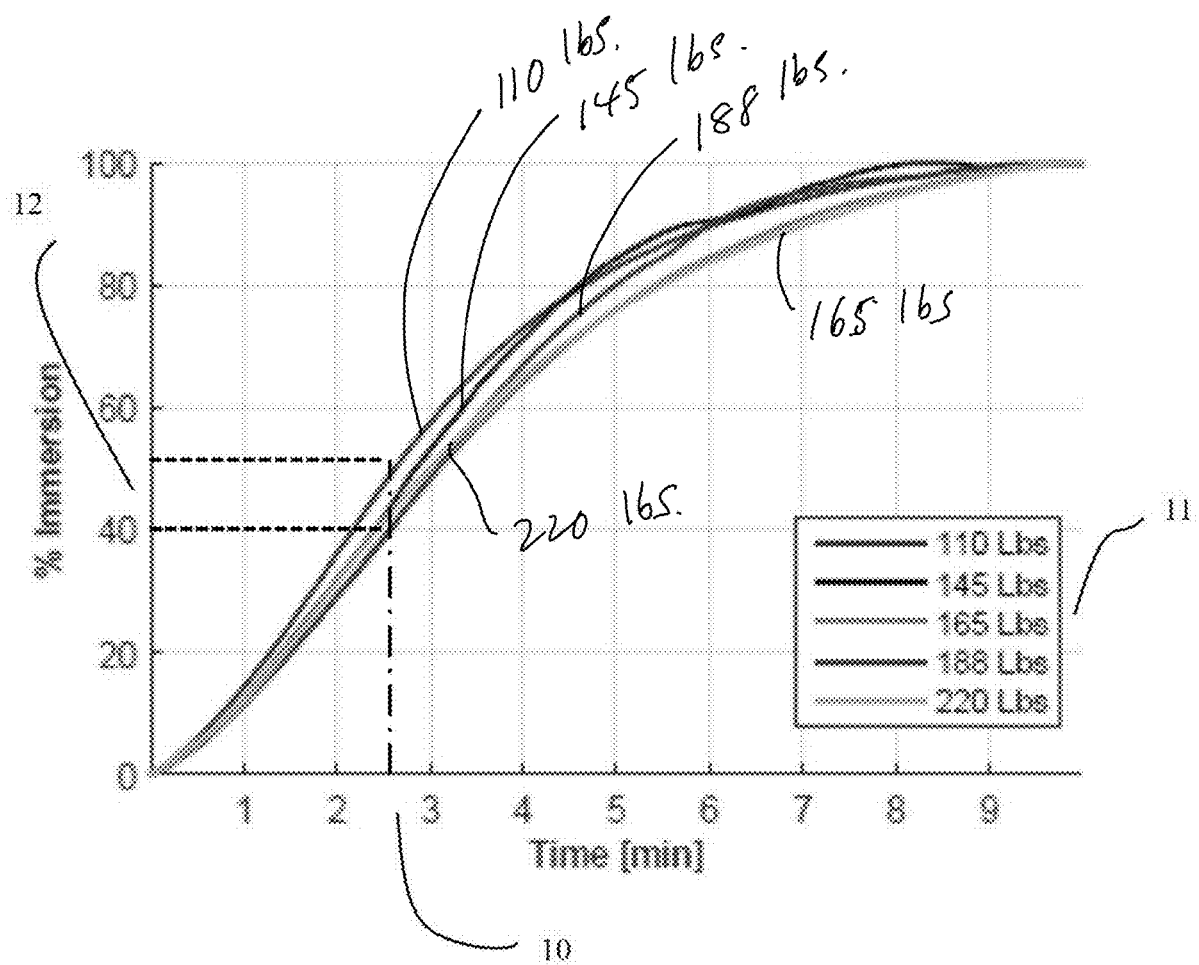
Figure 2:
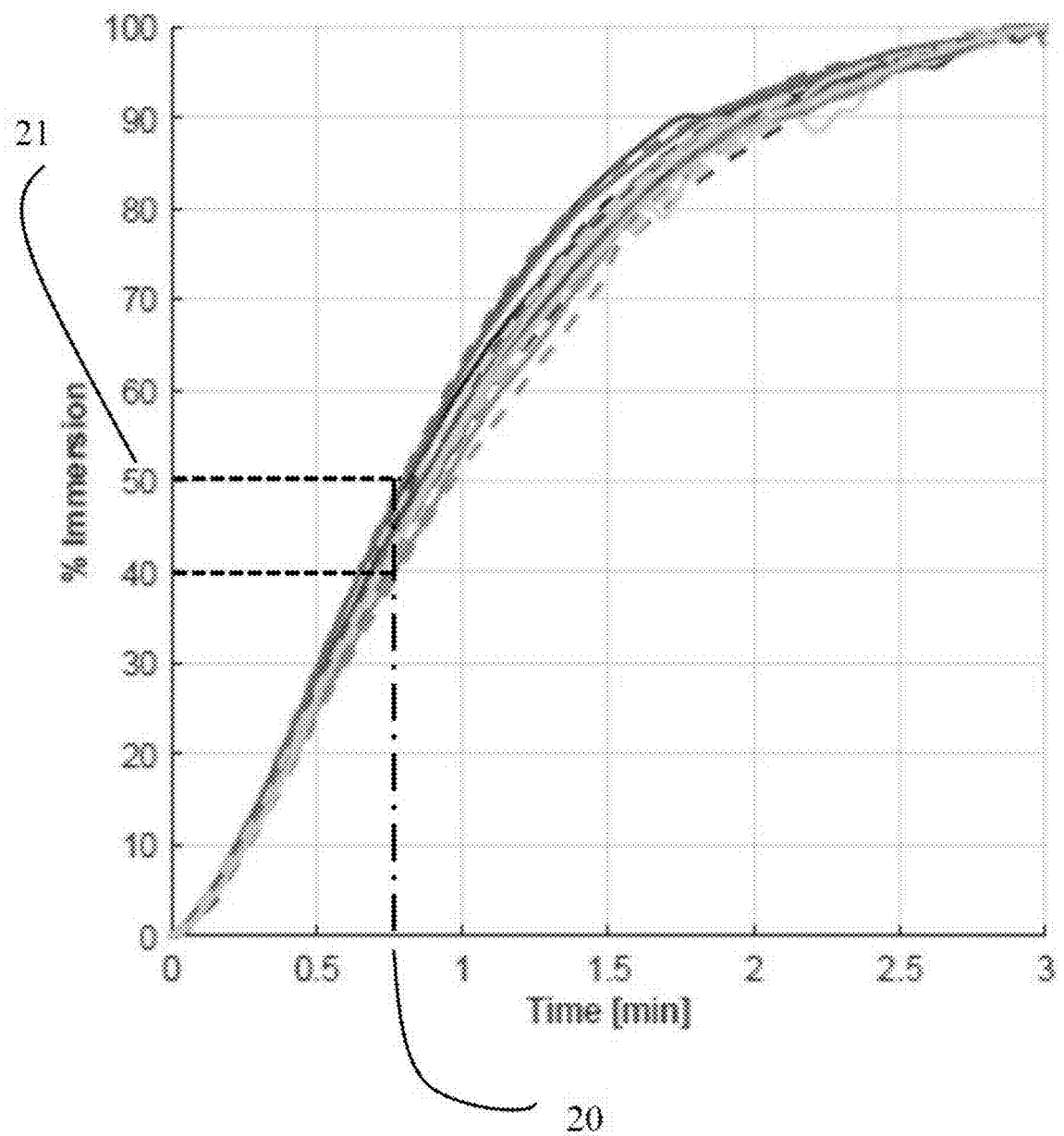

As an example, for a given configuration of air-filled chambers that were of height 88.9 mm that comprised a support surface, the chambers were filled to 60 mmHg. FIG. 1 shows that after slowly exhausting (average exhaust rate approximately 5.8 LPM) for 2.5 minutes 10 all subjects tested across a defined weight range of 110-220 lbs. (49.9-99.8 kg) 11 fall between 40 and 50% immersion 12. FIG. 2 shows that after quickly exhausting (average exhaust rate approximately 19.2 LPM) for 45 seconds 20 all subjects again fall between 40 and 50% immersion 21. Once the timed exhaust has been completed, the individual was at the desired immersion level ±12.7 mm. The exhaust rate for a given support surface configuration is a function of the current fluid pressure in the system, the load on the system, and the mechanical and material properties of the fluid transport systems (i.e., tubes, valves, connectors). The time to desired immersion is also a function of the volume of fluid in the system prior to beginning the Timed Exhaust method. The results from the experimental data presented here are not rank ordered by individual weight.

The Timed Exhaust method is not limited to the weight range in the example above, and can be used for all weight ranges, to include neonatal infants to bariatric patients. Variance in the % immersion as a function of time can be attributed to differences in initial pressure in any chamber from its desired initial chamber pressure, measurement error, individual location on the support surface, mass distribution of the individual, as examples.

A further method of the present invention includes maintaining the desired immersion level of the patient within specified bounds over time. When the patient is initially immersed to a desired immersion level, a set point reading is taken from the one or more chambers in the support surface to be used as a reference for maintaining that level of immersion to within a desired range from the set point for that chamber, such as ±1 mmHg. Alternatively, other measurement methods can be employed to quantify the current immersion level, such as a depth sensor, RFID tag, or optical systems, among others. The set point can be either a single measurement or a series of measurements with the results averaged, and can be recorded either automatically or manually. The set point could be modified manually for comfort, if desired.

A method of the present invention includes employing a therapy that further seeks to reduce TIP. The method is directed to actively and continuously redistributing pressure from the patient's tissues when on a support surface, herein called Targeted Offloading, to a desired set point, such as pressure or depth. In one embodiment of the present invention, pressure can be redistributed from specific zones of the surface. An area of the support surface, which may encompass one or more chambers, or group of chambers, with high TIP will typically have different offloading than areas of lower TIP. Different offloading may infer offloading occurs more or less often, at a higher or lower priority, for a longer or shorter duration, or at a faster or slower rate. Chamber-based or external sensors are useful to determine the local TIP.

Further, in the present invention, adaptive task scheduling is employed for parametric control of chambers or groups of chambers based on a scoring system employing sensor measurements. In further embodiments of the present invention, real-time dynamic task prioritization based on at least one time-based value and one or more sensors measuring parameter(s) of interest is employed. In certain embodiments of the present invention sensors include, but are not limited to, those for pressure, temperature, humidity, tissue density, or microclimate control.

One example of Targeting Offloading employs a scoring system that is used to rank order the priority for which the various chambers in the support surface are offloaded. The scoring system of the present method can be described as static or active. An example of a static scoring uses the set point for each chamber and assigning an offloading order based on that set point. The location of that chamber within the surface could be a variable used to set the offloading order. A combination of set point and location could be used. A combination of time and location could be used. An example of an active scoring system uses chamber set point, and chamber location as initial parameter to assign an initial order for offloading, and time since that chamber was last offloaded to modify the order for offloading during therapy. Additional parameters can be added, such as patient location, specific regions of the body, and other physiologic or environmental parameters, alone or in combination with each other. Visual indicators or alarms can display support surface performance, including immersion and offloading status.

A novel approach to managing offloading of tissue creates a chamber offloading algorithm based on variables including but not limited to an assigned chamber priority level 30, load on a chamber, and time since that chamber was last offloaded. This algorithm can be applied to an individual chamber or groups of chambers, each called a chamber group. An offloading score is generated for each chamber group, and that score is used to prioritize offloading of that chamber group. For example, in one embodiment, an of an active scoring system is given by offloading scores calculated as Chamber Group Offloading Score=(Chamber Group Priority×Load)+Time since last offload where:

OFFLOADING SCORE=(CELL PRIORITY×LOAD)+DURATION

Where:

$$\text{CELL PRIORITY} = \begin{cases} 1: \text{Low} \\ 2: \text{Medium} \\ 3: \text{High} \end{cases}$$

$$\text{LOAD} = \begin{cases} 1: \text{Low} \\ 2: \text{Medium} \\ 3: \text{High} \end{cases}$$

DURATION=# of consecutive offloading periods for which cell has been loaded

Figure 3:
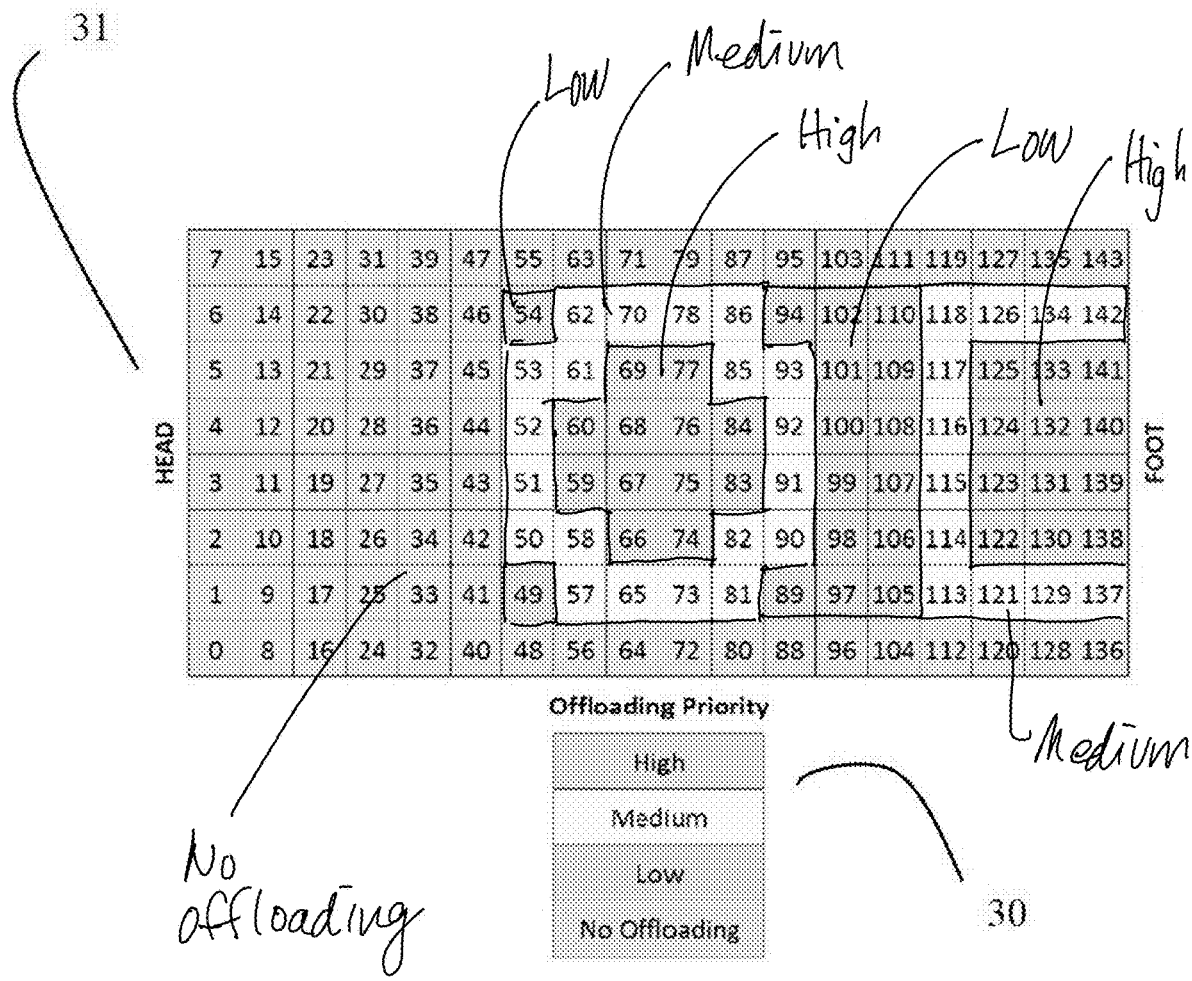
FIG. 3 is an exemplar map of chamber group priorities for an array of chambers.

An exemplar map of chamber group priorities 30 for an array or chambers 31 is shown in FIG. 3.

Figure 4A:
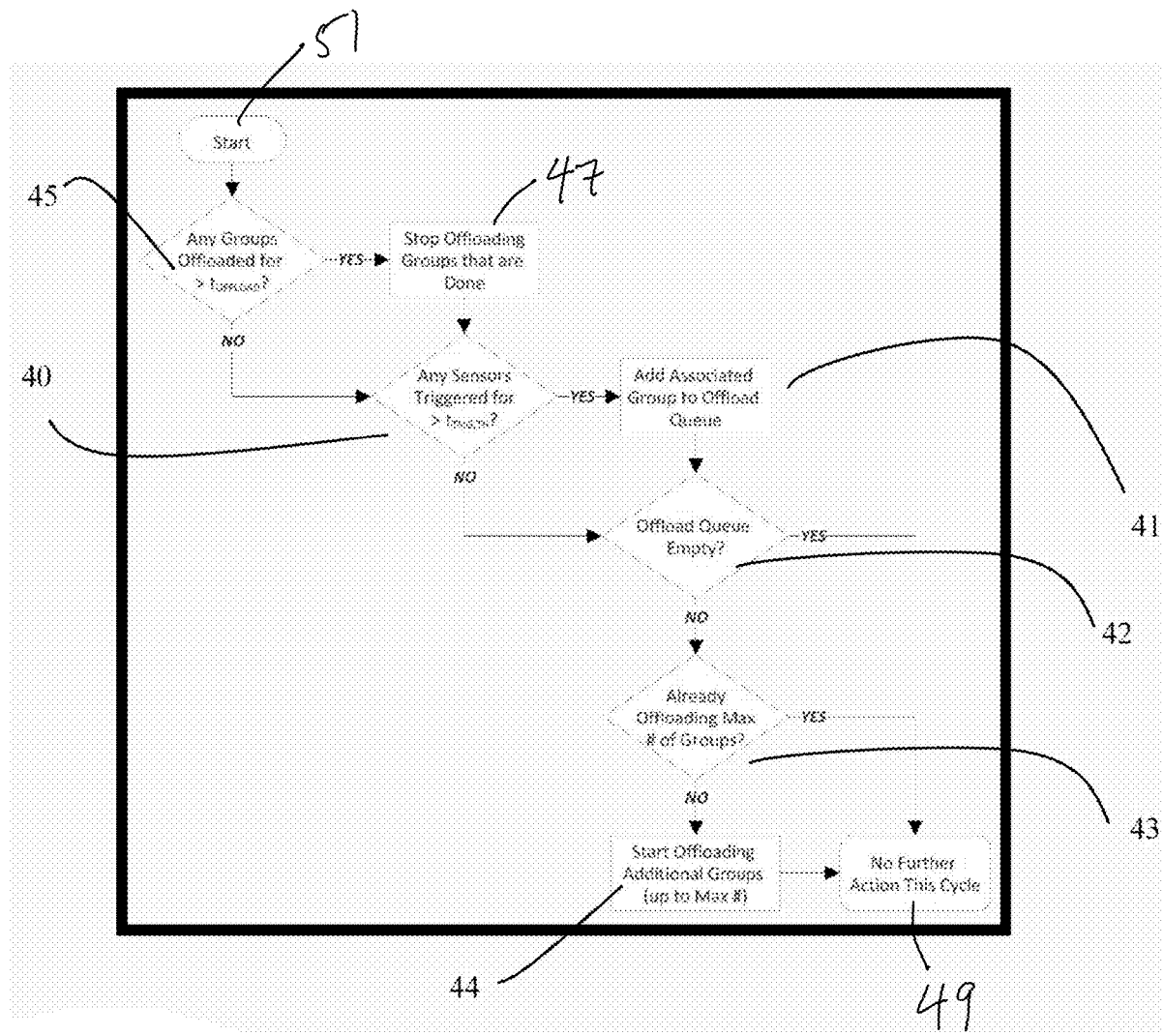
FIG. 4a is a flow diagram of a targeted offloading algorithm and scoring system for offloading.

Once a chamber or chamber group is identified for offloading, it is offloaded for a fixed period of time, or until a lower pressure is reached, as part of the Targeted Offloading method. An offloading period can be defined as a number of seconds for which loaded chambers will be offloaded. A flow diagram of a Targeted Offloading algorithm and scoring system for offloading is provided in FIG. 4*a*. After the chambers are offloaded, they are allowed to return to their original set point pressure and maintained at the desired immersion set point as described above and shown in FIG. 4*b*.

In one embodiment, the offloading system monitors when a chamber or group of chambers has been loaded/triggered for a time $>t_{trig,th}$ 40. The chamber groups associated with any sensors meeting this threshold condition are placed into an offloading queue 41 which is examined at a time interval. When the offload queue is not empty 42, the system offloads as many groups as possible 43 while keeping the total number of currently-offloading groups $\leq n_{offload,max}$ 44. If already offloading a maximum number of groups, then no further action is needed on this cycle at 49. Selection of priority for offloading chambers or chamber groups can be FIFO or randomly selected from the queue; additional restrictions on simultaneous offloading (e.g. adjacent groups) may be required. The system offloads a chamber group for $>t_{offload}$ 45 after a cycle is started at 51. If there are any groups that are offloaded for $>t_{offload}$, then stop offloading groups that are done at 47.

Figure 4B:
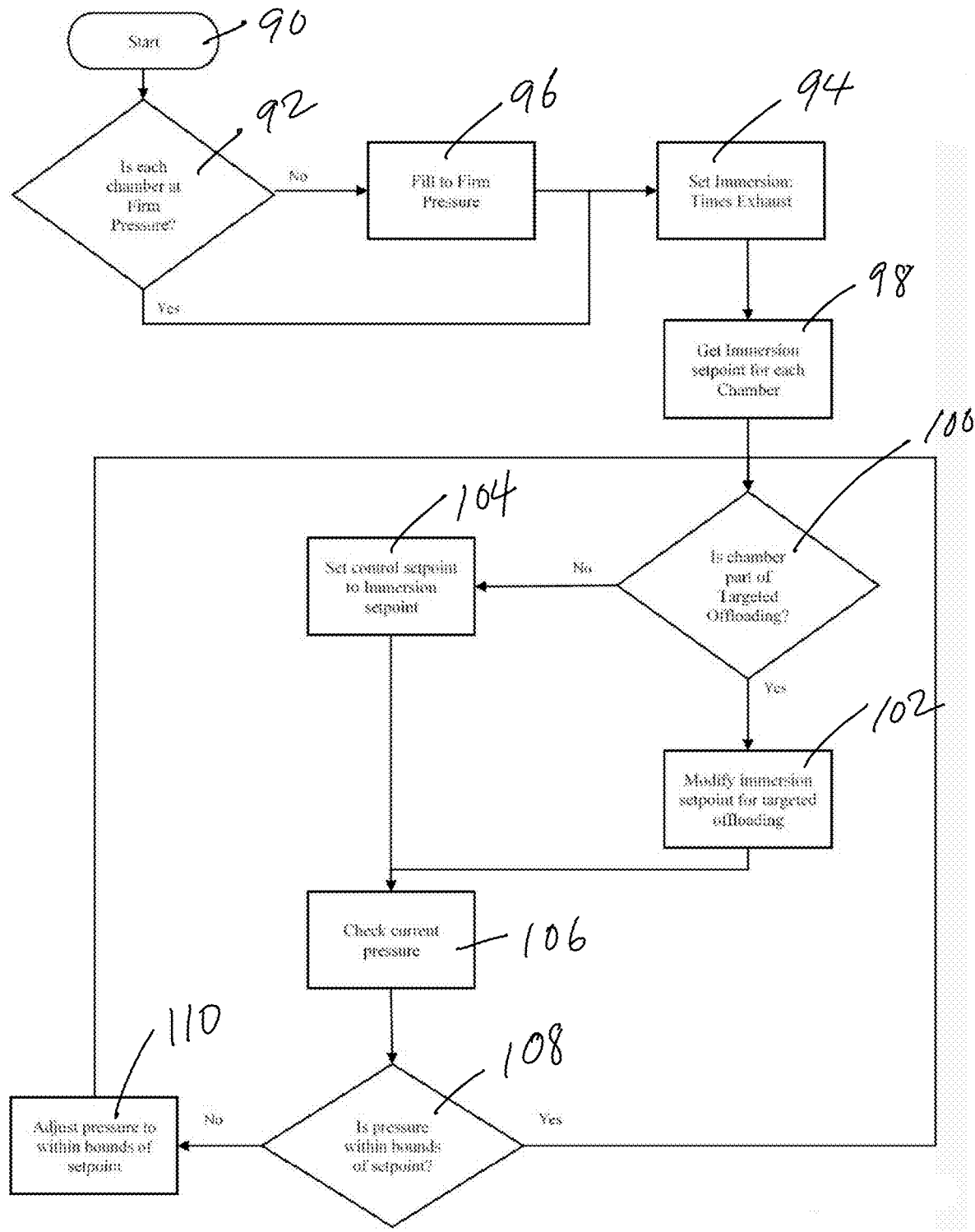
FIG. 4b shows a flow diagram where, after the chambers are offloaded, they are allowed to return to their original set point pressure and maintained at the desired immersion set point.

In FIG. 4*b*, the cycle is started at 90. If each chamber is at firm pressure at 92, then set immersion: times exhaust at 94. If not, fill form to pressure at 96. Then, get immersion setpoint for each chamber at 98. If the chamber is part of targeted offloading at, then modify immersion setpoint for targeted offloading at 102. If not, set control setpoint to immersion setpoint at 104. Then, check the current pressure at 106. If the pressure is not within the bounds of the setpoint at 108, then adjust the pressure at 110.

Additional constraints can be added to the algorithm to include limitations on the numbers of chamber groups that should be offloaded at any time, their adjacencies—adjacent cells may be increased in order maintain immersion at the set point, for example. In one embodiment, for example, the following constraints can be used in developing the scoring system and queue for offloading.

Only 4 chambers/groups may be offloaded at any given time

Adjacent chambers/groups (those that share an edge) may not be offloaded simultaneously Additional control of the immersion to the desired level is accomplished by detecting position changes of the individual by sensing means, including but not limited to monitoring cell pressure and/or with other sensing means on, in, or under the support surface. Set points are adjusted and scaled from their original value when a patient moves after the Timed Exhaust.

Figure 5:
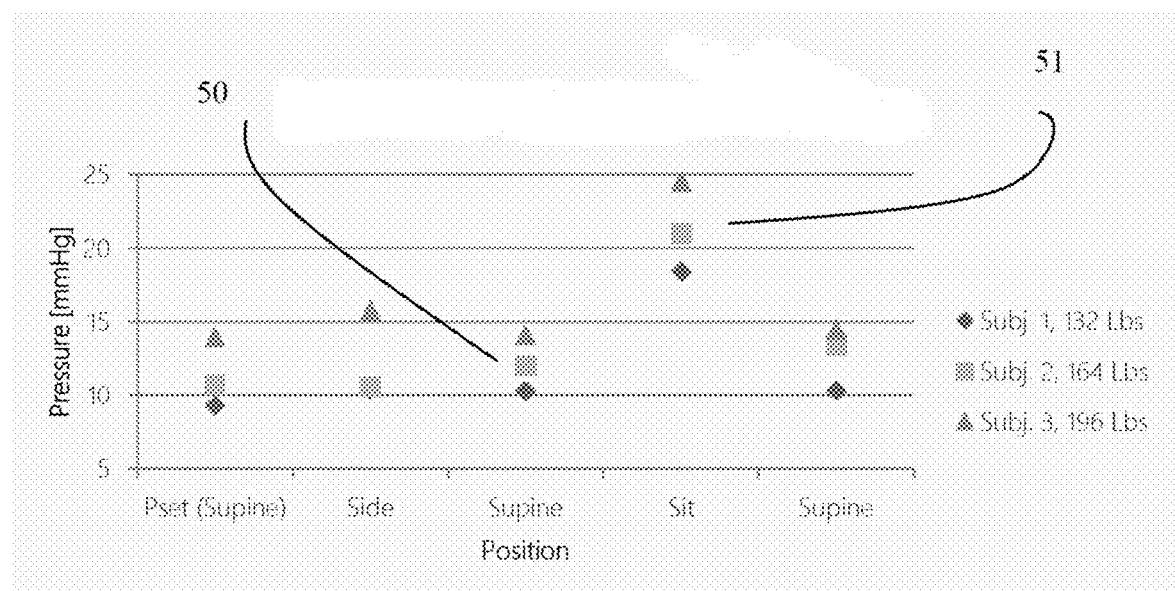
FIG. 5 is a graph showing significant increase in pressure when the patients changed states from supine to sitting.
Figure 6:
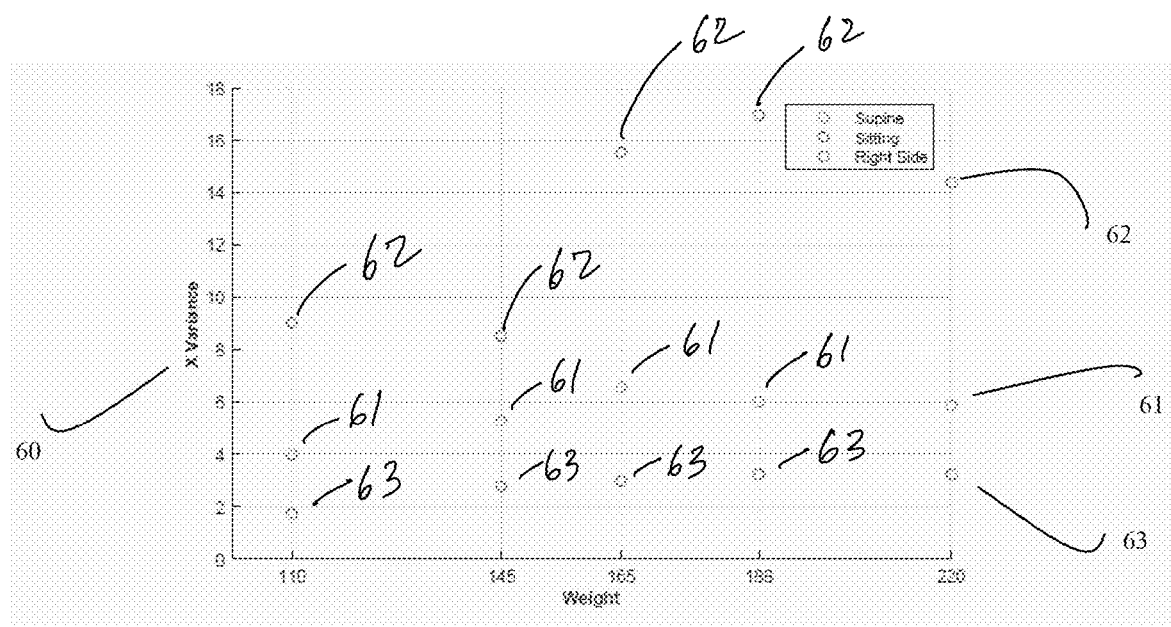
FIG. 6 is a graph showing identified changes of +/−30% in variance of triggered chambers in the direction of the length of the support surface.
Figure 7:
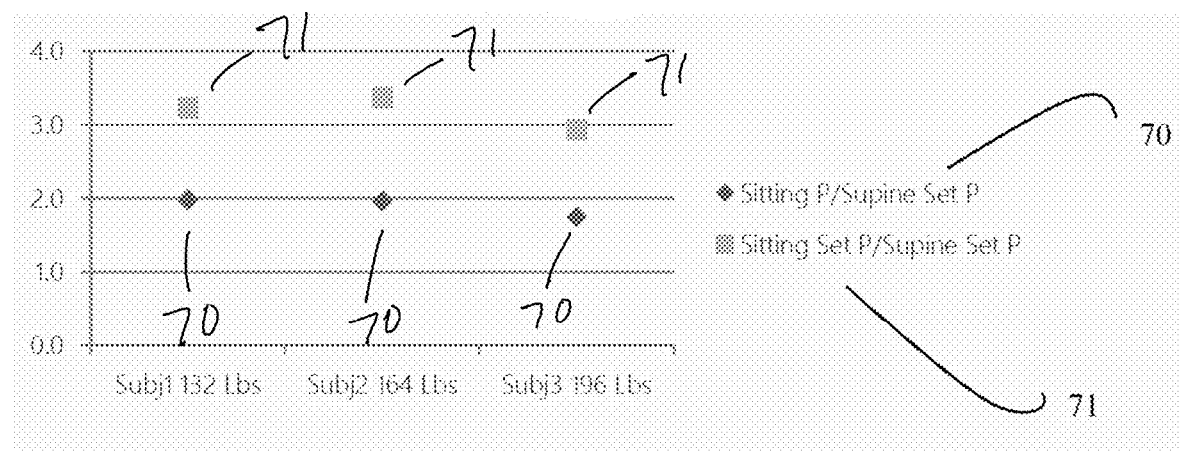
FIG. 7 is a graph showing the relative pressure of a subject who changes states from supine to sitting and the relative pressure required to make the subject feel comfortably immersed while sitting.

As an example, chamber pressure can be monitored during after Timed Exhaust. In an experiment, there was a significant increase in pressure when the patients changed states from supine 50 to sitting 51 (FIG. 5). Changes of +/−30% in variance of triggered chambers in the direction of the length of the support surface 60 were identified (FIG. 6) and correlated with a change in position. A change of +30% indicated a change from supine 61 to side 62, while a change of −30% indicated a change from supine 61 to sitting 63. A position change could be used to identify the need for a change in desired set point for that chamber or group of chambers. In some cases, this change in set point might only be adjusted for a state change to/from the sitting position. Often, subjects are well immersed at the supine set pressure. FIG. 7 shows the relative pressure of a subject who changes states from supine to sitting 70 and the relative pressure required to make the subject feel comfortably immersed while sitting 71.

By monitoring chambers along the edge (lengthwise) of the surface which are held at a fixed pressure (not part of the chambers used for immersion control), we can detect an increase in pressure when a visitor sits on the edge of the surface and then adjust the pressure of the surrounding chambers to support both the patient and the visitor. This offset/scaling can be removed when the visitor leaves.

The individual on a support surface and their location on that support surface after Timed Exhaust uses the set point to define a profile of the individual on the support surface. The profile can be based on one or more variables including but not limited to pressure, or immersion depth for each chamber or group of chambers that comprise the support surface. For example, the profile can be a pressure profile. From this profile, anatomic structures can be identified such as the head, foot, and other prominent features of the patient. The profile can be tracked over time to indicate patient location or location of prominent features of the patient on the support surface for further reduction of TIP using methods that could include Targeted Offloading. Additional parameters that can be determined from the patient profile include frequency of patient movement or prominent feature movement to quantify mobility, and sleep quality, among others, of the individual on the support surface, and activity of the individual on the support surface as a result of their moving or to caregiver interaction that leads to the individual moving on the support surface.

Monitoring the dynamic pressures of a person on a support surface, one can extract important physiological parameters such as heart rate or respiratory rate. As the heart beats or lungs fill, small changes in pressure on the support surface can be detected. In combination with time series data decimation techniques such as Independent Component Analysis (ICA) or Principal Component Analysis (PCA), these small changes can be extracted and amplified due to the effects heart rate and respiratory rate will be seen in most bladders.

Another embodiment may adjust set points of bladders to increase pressures within these bladders to prevent patient migration. It is well known that if the bed is articulated to allow a patient to be in a seated position, the patient will slowly slide down the bed. By increasing the bladder pressures below the buttock region will help engage the patient better and prevent patient migration while still providing immersion.

Another embodiment may seek to identify if an individual has exited the support surface by monitoring changes to the set point after initial immersion. If, for example, pressure sensors are used, then a large change in the current pressure from non-zero to values that are near-zero would indicate there is no load on the surface and the individual is out of bed.

The present invention is provided to solve the problems discussed above and other problems, and to provide advantages and aspects not provided by prior systems of this type. A full discussion of the features and advantages of the present invention is deferred to the following detailed description, which proceeds with reference to the accompanying drawings.

What is claimed is:

1. A method for reducing tissue interface pressure on a support surface, the method comprising the steps of:
   providing a support surface having one or more fluid chambers;
   exhausting fluid from the one or more fluid chambers of the support surface from a known starting pressure in each of the one or more fluid chambers for a fixed time to achieve a desired level of immersion into the surface;
   taking a set point reading from the one or more fluid chambers in the support surface to be used as a reference for maintaining the desired level of immersion to within a desired range from the set point for that chamber;
   maintaining the desired immersion level of an individual in contact with the support surface within specified bounds over time;
   actively and continuously redistributing pressure from tissues of the individual when on the support surface to the set point by redistributing the fluid from the one or more fluid chambers;
   wherein the redistribution of fluid from the one or more fluid chambers occurs is controlled by adaptive task scheduling for the one or more fluid chambers based on a scoring system; and
   wherein the scoring system is static using the set point for each of the one or more fluid chambers and assigning an offloading order based on the set point.

2. The method of claim 1, wherein the adaptive task scheduling for control of the one or more fluid chambers is based on time.

3. The method of claim 1, wherein the adaptive task scheduling is based on at least one time-based value and measurement from at least one sensor.

4. The method of claim 3, wherein the at least one sensor measures one or more of pressure, temperature, humidity, tissue density, or microclimate.

5. The method of claim 1, wherein the scoring system is based on sensor measurements.

6. The method of claim 1, wherein the scoring system uses the set point for each chamber to assign an order for redistribution of the fluid from the one or more fluid chambers.

7. The method of claim 1, wherein the scoring system uses the location of the one or more fluid chambers on the support surface to assign an order for redistribution of the fluid from the one or more fluid chambers.

8. The method of claim 1, wherein the scoring system uses the set point for each of the one or more fluid chambers and the location of the one or more fluid chambers on the support surface to assign an order for redistribution of the fluid from the one or more fluid chambers.

9. The method of claim 1, wherein the scoring system uses location data of the one or more fluid chambers on the support surface and time to assign an order for redistribution of the fluid from the one or more fluid chambers.

10. The method of claim 1, wherein the scoring system uses the set point for each of the one or more fluid chambers, the location of the one or more fluid chambers on the support surface, and time to assign an order for redistribution of the fluid from the one or more fluid chambers.

11. The method of claim 1, wherein the wherein an offloading system monitors when one of the one or more fluid chambers has been loaded or triggered for a time $>t_{trig,th}$.

12. A method for reducing tissue interface pressure on a support surface, the method comprising the steps of:

providing a support surface having one or more fluid chambers;

exhausting fluid from the one or more fluid chambers from a known starting pressure in each chamber for a fixed time to achieve a desired level of immersion into the surface;

taking a set point reading from the one or more fluid chambers in the support surface to be used as a reference for maintaining the desired level of immersion to within a desired range from the set point for that chamber;

maintaining the desired immersion level of a patient within specified bounds over time;

actively and continuously redistributing pressure from the patient's tissues when on a support surface to the set point by redistributing the fluid from the one or more fluid chambers;

wherein the redistribution of fluid from the one or more fluid chambers occurs is controlled by adaptive task scheduling for the one or more fluid chambers based on a scoring system;

wherein the scoring system is static using the set point for each of the one or more fluid chambers and assigning an offloading order based on the set point; and returning the one or more fluid chambers to the set point after redistribution of fluid from the one or more fluid chambers.

* * * * *